US010806365B2

(12) United States Patent
Gliner

(10) Patent No.: US 10,806,365 B2
(45) Date of Patent: Oct. 20, 2020

(54) IMPEDANCE-BASED POSITION TRACKING PERFORMANCE USING PRINCIPAL COMPONENT ANALYSIS

(71) Applicant: Biosense Webster (Israel) Ltd., Yokneam (IL)

(72) Inventor: Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 398 days.

(21) Appl. No.: 15/854,078

(22) Filed: Dec. 26, 2017

(65) Prior Publication Data
US 2019/0192042 A1 Jun. 27, 2019

(51) Int. Cl.
*A61B 5/053* (2006.01)
*A61B 8/00* (2006.01)
*A61B 8/08* (2006.01)
*A61B 5/06* (2006.01)
*A61B 8/12* (2006.01)
(Continued)

(52) U.S. Cl.
CPC .......... *A61B 5/0536* (2013.01); *A61B 5/062* (2013.01); *A61B 5/063* (2013.01); *A61B 8/4254* (2013.01); *A61B 8/483* (2013.01); *A61B 5/743* (2013.01); *A61B 8/12* (2013.01); *A61B 2017/00243* (2013.01); *A61B 2034/2053* (2016.02); *A61B 2034/2072* (2016.02); *A61B 2560/0238* (2013.01)

(58) Field of Classification Search
CPC ....... A61B 5/062; A61B 5/063; A61B 8/4254; A61B 8/483; A61B 5/0536; A61B 8/12; A61B 2034/2072; A61B 2560/0238; A61B 5/743; A61B 2034/2053; A61B 2017/00243

USPC .................................................. 600/424, 407
See application file for complete search history.

(56) References Cited

U.S. PATENT DOCUMENTS 5,184,620 A * 2/1993 Cudahy .............. A61B 5/04085
600/382
5,391,199 A 2/1995 Ben-Haim
(Continued)

FOREIGN PATENT DOCUMENTS

WO WO 96/05768 A1 2/1996

OTHER PUBLICATIONS

European Extended Search Report dated May 6, 2019 for corresponding EP Application No. 18215625.7.
(Continued)

*Primary Examiner* — Oommen Jacob

(57) ABSTRACT

An apparatus includes an interface and a processor. The interface is configured to receive signals from a calibration probe inserted in an organ of a patient. The processor is configured to hold multiple electrode positions corresponding respectively to multiple electrodes attached externally to the patient, to evaluate, based on the received signals, multiple data points, each data point including (i) a respective measured coordinate of the calibration probe, and (ii) a respective set of electrical values indicative of respective impedances between the calibration probe and the multiple electrodes. The processor is further configured to evaluate, based on the multiple data points and on the electrode positions, an alternative position for a selected electrode to be repositioned, and to output an identification of the selected electrode and the evaluated alternative position.

6 Claims, 4 Drawing Sheets

(51) Int. Cl.
  *A61B 5/00*   (2006.01)
  *A61B 34/20*  (2016.01)
  *A61B 17/00*  (2006.01)

(56) References Cited

U.S. PATENT DOCUMENTS

| | | | | |
|---|---|---|---|---|
| 5,437,279 | A * | 8/1995 | Gray | A61B 10/00 |
| | | | | 128/898 |
| 5,697,377 | A * | 12/1997 | Wittkampf | A61B 5/042 |
| | | | | 128/899 |
| 6,239,724 | B1 | 5/2001 | Doron et al. | |
| 6,332,089 | B1 | 12/2001 | Acker et al. | |
| 6,484,118 | B1 | 11/2002 | Govari | |
| 6,618,612 | B1 | 9/2003 | Acker et al. | |
| 6,690,963 | B2 | 2/2004 | Ben-Haim et al. | |
| 7,341,954 | B2 * | 3/2008 | Yamazaki | H01J 37/32935 |
| | | | | 216/58 |
| 8,456,182 | B2 | 6/2013 | Bar-Tal et al. | |
| 2002/0065455 | A1 | 5/2002 | Ben-Haim et al. | |
| 2003/0120150 | A1 | 6/2003 | Govari | |
| 2005/0288586 | A1 * | 12/2005 | Ferek-Petric | A61B 8/0833 |
| | | | | 600/443 |
| 2007/0050076 | A1 * | 3/2007 | Yamazaki | H01J 37/32935 |
| | | | | 700/121 |
| 2008/0009711 | A1 * | 1/2008 | Govari | A61B 5/06 |
| | | | | 600/424 |
| 2009/0030469 | A1 * | 1/2009 | Meiry | A61N 1/025 |
| | | | | 607/4 |
| 2010/0079158 | A1 * | 4/2010 | Bar-Tal | A61B 5/06 |
| | | | | 324/705 |
| 2010/0198638 | A1 * | 8/2010 | Deffenbaugh | G01V 11/00 |
| | | | | 705/308 |
| 2010/0198900 | A1 * | 8/2010 | Gifford | G06K 9/6218 |
| | | | | 708/401 |
| 2011/0054293 | A1 | 3/2011 | Markowitz et al. | |
| 2011/0092809 | A1 | 4/2011 | Nguyen et al. | |
| 2011/0118803 | A1 * | 5/2011 | Hou | A61B 5/04011 |
| | | | | 607/17 |
| 2011/0160801 | A1 * | 6/2011 | Markowitz | A61B 5/0028 |
| | | | | 607/60 |
| 2011/0288605 | A1 * | 11/2011 | Kaib | A61B 5/1118 |
| | | | | 607/5 |
| 2012/0172702 | A1 | 7/2012 | Koyrakh et al. | |
| 2013/0066193 | A1 * | 3/2013 | Olson | A61B 5/062 |
| | | | | 600/424 |
| 2015/0126895 | A1 | 5/2015 | Lichtenstein | |
| 2015/0141798 | A1 | 5/2015 | Bar-Tal | |
| 2016/0256066 | A1 * | 9/2016 | Chetelat | A61B 5/04085 |
| 2016/0296171 | A1 * | 10/2016 | Drori | A61B 5/053 |
| 2016/0331268 | A1 * | 11/2016 | Hauck | A61B 5/042 |
| 2017/0301102 | A1 | 10/2017 | Urman et al. | |
| 2019/0192042 | A1 * | 6/2019 | Gliner | A61B 5/062 |

OTHER PUBLICATIONS

Wold, Svante et al., "Principal Component Analysis" Chemometrics and Intelligent Laboratory Systems, (1987), pp. 37-52, vol. 2.

* cited by examiner

IMPEDANCE-BASED POSITION TRACKING PERFORMANCE USING PRINCIPAL COMPONENT ANALYSIS

FIELD OF THE INVENTION

The present invention relates generally to position tracking of medical probes, and particularly to methods and systems for improving the accuracy and sensitivity of an impedance-based position tracking system.

BACKGROUND OF THE INVENTION

Various tracking techniques, such as active current location (ACL) and magnetic position sensing, may be used for tracking the position of a medical probe in a patient body.

For example, U.S. Patent Application Publication 2011/0092809 describes a method that includes accessing cardiac information acquired via a catheter located at various positions in a venous network of a heart of a patient. The cardiac information comprises position information with respect to time for one or more electrodes of the catheter. Performing a principal component analysis on at least some of the position information, and selecting at least one component of the principal component analysis to represent an axis of a cardiac coordinate system.

U.S. Patent Application Publication 2012/0172702 describes a system for determining a location of an electrode of a medical device (e.g., a catheter) in a body of a patient. The system includes a localization block for producing an uncompensated electrode location, a motion compensation block for producing a compensation signal (i.e., for respiration, cardiac), and a mechanism for subtracting the compensation signal from the uncompensated electrode location.

SUMMARY OF THE INVENTION

An embodiment of the present invention that is described herein provides an apparatus including an interface and a processor. The interface is configured to receive signals from a calibration probe inserted in an organ of a patient. The processor is configured to hold multiple electrode positions corresponding respectively to multiple electrodes attached externally to the patient, to evaluate, based on the received signals, multiple data points, each data point including (i) a respective measured coordinate of the calibration probe, and (ii) a respective set of electrical values indicative of respective impedances between the calibration probe and the multiple electrodes. The processor is further configured to evaluate, based on the multiple data points and on the electrode positions, an alternative position for a selected electrode to be repositioned, and to output an identification of the selected electrode and the evaluated alternative position.

In some embodiments, the data points are representable as a three-dimensional (3D) cluster, and the processor is configured to evaluate the alternative position by projecting the 3D cluster onto a selected two-dimensional (2D) coordinate system. In other embodiments, the 2D coordinate system includes first and second axes, and the processor is configured to evaluate the alternative position by evaluating a 2D cluster produced by projected data points relative to the first and second axes.

In an embodiment, the 2D cluster includes an ellipse whose axes are defined by the first and second axes, and the processor is configured to evaluate the alternative position by calculating a ratio between lengths of the first and second axes within the 2D shape. In another embodiment, the processor is configured to evaluate the alternative position by applying principal component analysis (PCA) to the data points. In yet another embodiment, the interface is configured to derive the respective measured coordinate of the calibration probe from a signal received from a magnetic position sensor in the calibration probe.

There is additionally provided, in accordance with an embodiment of the present invention, a method that includes receiving signals from a calibration probe inserted in an organ of a patient. Multiple electrode positions, corresponding respectively to multiple electrodes attached externally to the patient, are held. Based on the received signals, multiple data points are evaluated, each data point including (i) a respective measured coordinate of the calibration probe, and (ii) a respective set of electrical values indicative of respective impedances between the calibration probe and the multiple electrodes. Based on the multiple data points and on the electrode positions, an alternative position for a selected electrode to be repositioned is evaluated. An identification of the selected electrode and the evaluated alternative position is output.

The present invention will be more fully understood from the following detailed description of the embodiments thereof, taken together with the drawings in which:

DETAILED DESCRIPTION OF EMBODIMENTS

Overview

Figure 1:
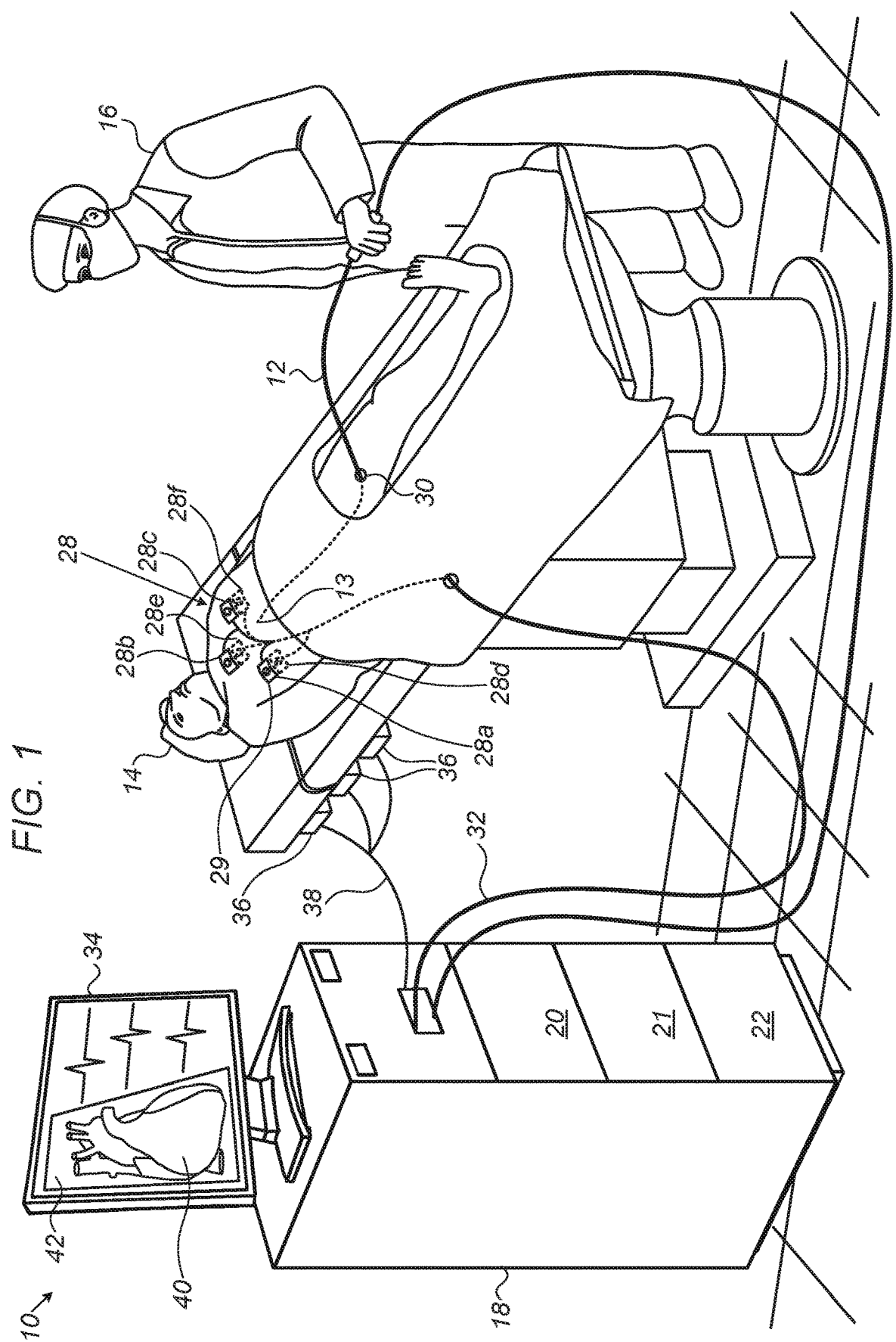
FIG. 1 is a schematic, pictorial illustration of a system for electro-potential (EP) mapping tissue of a patient heart, in accordance with an embodiment of the present invention.

Embodiments of the present invention that are described hereinbelow provide techniques for improving accuracy and sensitivity of impedance-based mapping and position tracking.

In some embodiments, a bio-impedance measuring system, such as an active current location (ACL) system, is used in tracking the position of a catheter, or another medical probe, in a patient body. In ACL, tracking the catheter is typically based on measuring impedances between the catheter and external body electrodes. Each measurement is then translated into a respective position of the catheter within the body. The translation is typically based on a suitable mapping, which is constructed beforehand and translates electrical values indicative of respective impedances, measured using the electrodes, into a respective position of the catheter.

In the context of the present disclosure and in the claims, the term "electrical value" refers to impedance, current, voltage or to any other suitable electrical value indicative of the impedance.

The design of the mapping is important for achieving high position tracking performance, such as lateral resolution and position accuracy between the actual position of the catheter and the position reported by the ACL system.

In some embodiments, the mapping is constructed using a calibration probe comprising two types of sensors: a magnetic position sensor of a magnetic position tracking system, and a bio-impedance sensor of the ACL system. The calibration probe is configured to acquire multiple data points at multiple locations in a patient organ (e.g., heart). Each data point comprises a respective position of the probe measured by the magnetic position sensor, and multiple electrical values indicative of tissue impedance values between the probe within the patient body and respective electrodes attached to the patient skin. The collection of data points is referred to herein as the "mapping."

In a typical mapping construction procedure, an operator attaches three patches to the chest of the patient, and one or more patches to the back of the patient. Each patch comprises an external body electrode and a magnetic position sensor. One of the electrodes on a selected patch attached to the back of the patient serves as a reference electrode. In some embodiments, the mapping construction procedure is carried out by a processor that holds, in a memory, position values of the respective magnetic position sensors of the patches. In some embodiments, a physician places the calibration probe at multiple locations in the patient heart, and the calibration probe acquires one or more data points at each such location.

In some embodiments, the processor applies principal component analysis (PCA) techniques to evaluate the accuracy and sensitivity of the ACL system, based on the acquired respective data points and on the stored position values of the bio-impedance electrodes of respective patches.

In some embodiments, the processor is configured to check whether or not the sensitivity of the ACL system is within a specified value. When the processor determines that the ACL sensitivity is insufficient, one or more of the patches need to be repositioned, so as to improve the accuracy and sensitivity.

In some embodiments, the processor is configured to identify a selected electrode of a respective patch to be repositioned, and to evaluate an alternative position for the selected electrode on the patient body. The processor attempts to select the electrode, and the alternative position for the electrode, in a manner that is expected to yield the highest improvement in ACL accuracy and sensitivity. In some embodiments, the processor selects the electrode to be repositioned, and determines the alternative position for this electrode, by applying principal component analysis (PCA) to the previously-acquired data points.

In an embodiment, the processor is configured to display to a user an identification of the selected electrode and the suggested alternative position that provides improved accuracy and sensitivity of the ACL system compared to the position of the electrode prior to repositioning. The procedure of repositioning a selected electrode may be repeated multiple times until achieving acceptable ACL accuracy and sensitivity.

The disclosed techniques improve the quality of minimal invasive procedures by providing the physician with improved accuracy and sensitivity of the ACL position tracking system. Furthermore, the disclosed techniques reduce the cycle time of mapping procedures by indicating accurate placement of the patches on the patient body, instead of conventional trial and error methods currently carried out in mapping procedures.

System Description

FIG. 1 is a schematic, pictorial illustration of a system 10 for electro-potential (EP) mapping tissue of a patient heart 40, in accordance with an embodiment of the present invention. In some embodiments, system 10 supports constructing of a mapping, e.g., prior to ablation, for mapping heart 40 of a patient 14 as will be described in detail below, and using the constructed mapping for navigating a medical tool within heart 40, during an ablation procedure.

In some embodiments, system 10 comprises a medical probe, such as a catheter 12, comprising a distal tip 13 that comprises a plurality of devices (not shown), such as a magnetic position sensor, an impedance sensor, and optionally, an ablation electrode. In this configuration, catheter 12 with distal tip 13 is used as a calibration probe, as will be described below. During the mapping phase a physician 16 may insert catheter 12, via an insertion point 30, into vasculature of patient 14, and may then navigate the catheter tip to the patient's heart. Subsequently, catheter 12 is used for mapping tissue of heart 40 before ablating the tissue.

In some embodiments, an operating console 18 comprises a radiofrequency (RF) generator 22, configured to generate the RF ablation signals applied by catheter 12 on the tissue of heart 40.

In some embodiments, console 18 comprises a processor 20, typically a general-purpose computer, with suitable front end and interface circuits for receiving signals from catheter 12 and for controlling the other components of system 10 described herein. Processor 20 may be programmed in software to carry out the functions that are used by the system, and the processor stores data for the software in a memory (not shown). The software may be downloaded to console 18 in electronic form, over a network, for example, or it may be provided on non-transitory tangible media, such as optical, magnetic or electronic memory media. Alternatively, some or all of the functions of processor 20 may be carried out by dedicated or programmable digital hardware components.

In some embodiments, system 10 further comprises a magnetic position tracking system, and an impedance-based active current location (ACL) system. Each of these systems may be used for tracking the position of distal tip 13 for the purpose of navigating catheter 12 to ablation locations within heart 40 of patient 14.

In some embodiments, the magnetic position tracking system comprises magnetic field-generators 36 placed at known positions external to patient 14 e.g., below the patient's back. In an embodiment, console 18 assists in carrying out the techniques described herein.

In some embodiments, console 18 comprises a driver circuit 21, configured to drive field-generators 36 via a cable 38. When distal tip 13 is navigated by physician 16 into heart 40, the magnetic position sensor at distal tip 13, generates position signals in response to the sensed external magnetic fields produced by field-generators 36, thereby enabling processor 20 to identify the position of distal tip 13 within the cavity of heart 40.

The magnetic position sensor is connected to interface circuitry integrated with processor 20 at the catheter proximal end. In an embodiment, the position of distal tip 13 is shown on an image 42 of heart 40, which is displayed on a user display 34. In some embodiments, image 42 is acquired using an anatomical imaging system, such as a computerized tomography (CT) system or any other suitable imaging technique.

This method of magnetic-field based position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

As noted above, system 10 comprises an ACL system, which can serve as an alternative position tracking system to the magnetic-field based system. In some embodiments, the ACL system comprises a plurality of electrodes 28, which are coupled to the body of patient 14, e.g., via patches 29 that adhere to the skin of patient 14. In the example of FIG. 1, system 10 comprises six electrodes, of which electrodes 28a, 28b, and 28c are coupled to the front (e.g., chest) of patient 14, and electrodes 28d, 28e, and 28f are coupled to the back of patient 14.

As shown in FIG. 1, electrodes 28 are arranged in pairs as follows: electrodes 28a and 28d are facing one another on the right side of patient 14, electrodes 28c and 28f are facing one another on the left side of patient 14, and electrodes 28b and 28e are facing one another on the upper part of the chest and back of patient 14.

In other embodiments, system 10 may comprise any suitable number of electrodes, coupled to the patient skin in any suitable arrangement, as will be shown, for example in FIG. 2 below.

In an embodiment, a position sensor (not shown) of the magnetic position tracking system is coupled to each respective patch 29. In this embodiment, each position sensor produces a signal indicative of the position of a respective electrode 28 in the coordinate system of the magnetic position tracking system.

Electrodes 28 and respective position sensors of patches 29 are typically connected, via a cable 32, to processor 20, which is configured to receive position signals from the position sensors, and from electrodes 28 information such as values of impedance. Based on this information, to estimate the position of distal tip 13 within heart 40 using techniques that will be described below.

Display 34, is typically configured to facilitate performance of the mapping and/or ablation procedures by displaying relevant information to physician 16. For example, processor 20 may register between the coordinate systems of the aforementioned tracking systems and the coordinate system of the CT system (which acquired image 42), so as to display the location and orientation of distal tip 13 within image 42, e.g., by superimposing an icon representing distal tip 13 of catheter 12 over image 42 of heart 40.

As noted above, electrodes 28 are typically used for navigating catheter 12 within the body of patient 14, using impedance-based tracking techniques, such as those described, for example, in U.S. Pat. No. 8,456,182 and US Patent Application Publication 2015/0141798, whose disclosures are incorporated herein by reference. Such techniques involve estimating the location and orientation of distal tip 13 responsively to the different impedances measured between distal tip 13 and each of electrodes 28a-28f. As described above, the estimated location of distal tip 13 may be indicated to the physician as a suitable icon on display 34. Based on this indication, physician 16 may navigate distal tip 13 of catheter 12 to one or more desired locations within heart 40.

In some embodiments, the location and orientation of distal tip 13 at any given time, are typically estimated by applying an electrical signal of a known amplitude to distal tip 13, and the resulting voltage gradients and/or currents are measured at each pair of electrodes 28. In alternative embodiments, the electrical signal may be applied by electrodes 28, and the resulting electrical values are measured by distal tip 13.

In some embodiments, these applied electrical signals cause the pairs of electrodes 28 (e.g., pair of electrodes 28a and 28d, electrodes 28c and 28f, and electrodes 28b and 28e), each of which is located at a different position relative to the catheter, to exhibit different respective electrical values, due to a different amount of electrically-impeding tissue (and therefore, a different degree of impedance) between distal tip 13 and each of the pairs of electrodes 28.

In some embodiments, these measured electrical values are sent, via cable 32, to processor 20, which uses these values to estimate the relative location and orientation of distal tip 13 relative to electrodes 28 (whose positions are known). Alternatively, voltage gradients between the distal tip of the catheter and the electrodes may be generated, and the resulting currents flowing through the electrodes may be measured and used for estimating the location and orientation of distal tip 13.

As described above, physician 16 navigates distal tip 13 to visit at multiple locations within heart 40. In some embodiments, processor 20 is configured to receive from catheter 12 at each of the visited locations, two sets of values. The first set comprises position coordinates from the magnetic position tracking system, and the second set comprises one or more respective electrical values (e.g., a value of current or impedance from each pair of electrodes 28) from the ACL system.

In some embodiments, processor 20 is configured to construct a set of data points that each comprises the position and electrical values measured at a respective position visited by distal tip 13. This set of data points maps multiple selected electrical values into respective positions, and is referred to herein as "mapping." In an embodiment, when completed, the mapping is applied (e.g., during ablation) to electrical values acquired by distal tip 13 and/or electrodes 28, for translating measured electrical values into a position measurement in heart 40.

Note that a separate mapping may be constructed for selected respiration operations (for example, after a full inhalation operation, after a full exhalation operation, or a midpoint between inhalation and exhalation operations) of patient 14. In another embodiment, a separate mapping is constructed for each pair of electrodes.

Figure 2:
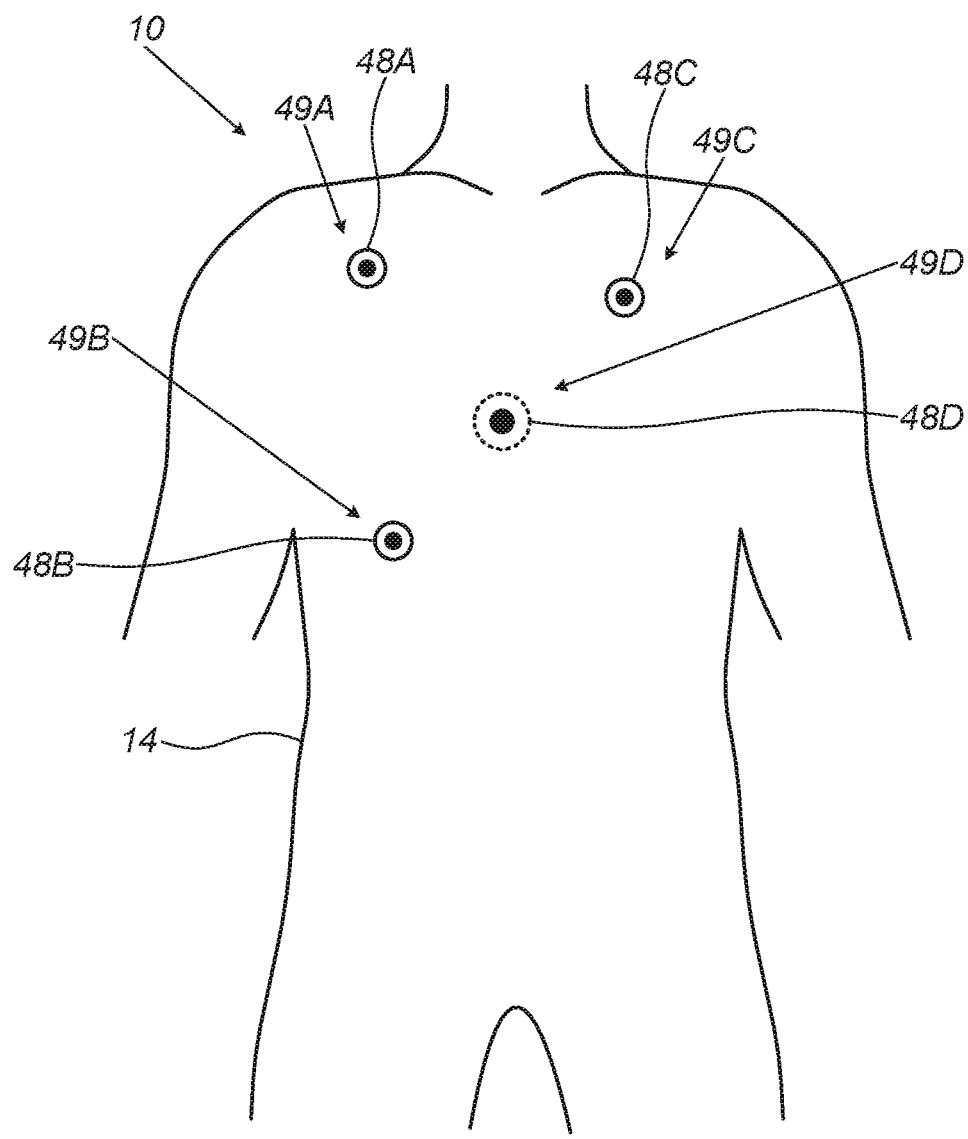
FIGS. 2 and 4 are schematic, pictorial illustrations of multiple electrodes attached externally to a patient body, in accordance with an embodiment of the present invention.

FIG. 2 is a schematic, pictorial illustration of patches 49A-49D of system 10 attached externally to the body of patient 14, in accordance with an embodiment of the present invention. Patches 49A-49D may correspond, for example, to patches 29A-29D of FIG. 1 above.

In some embodiments, patches 49A-49D comprise respective electrodes 48A-48D of the ACL system. Electrodes 48A-48D may correspond, for example, to respective electrodes 28A-28D of FIG. 1 above. In some embodiments, patches 49A-49D comprise respective position sensors (not shown), which are configured to provide the positions of respective electrodes 48A-48D in the coordinate system of the magnetic position system.

In the example of FIG. 2, electrodes 48A-48C coupled to respective patches 49A-49C are attached to the chest of patient 14, whereas electrode 48D, which serves as a reference electrode, is mounted on patch 49D coupled to the back of the patient. In alternative embodiments, system 10 may comprise any suitable number of electrodes (larger than three), such as electrodes 48A-48D, of which at least three electrodes are positioned on one side of patient 14 (e.g. on the chest) and at least one reference electrode is positioned on the other side (e.g. on the back) of patient 14.

In some embodiments, distal tip 13 of catheter 12 (FIG. 1) is configured to measure electrical values, indicative of respective voltage gradients or currents or impedances, between three pairs of electrodes, e.g., between each electrode 48A-48C, and reference electrode 48D. In these embodiments, the electrical signal applied between each pair of electrodes has a different frequency, so as to prevent interference between the electrical signals. For example, processor 20 may evaluate the impedance between electrodes 48A and 48D by measuring the impedance between distal tip 13 and each electrode 48A and 48D. In these embodiments, at each location of distal tip 13 within heart 40, processor 20 receives respective measurements of the electrical values and uses these measurements for calculating the location of distal tip 13 in heart 40.

In an embodiment, before inserting catheter 12 to heart 40, an operator (not shown) couples patches 49A-49C and reference patch 49D, respectively, to the chest and the back of patient 14. The position of patches 49A-49D, relative to heart 40 and to one another, determines a coordinate system having three axes. The angles between these axes determines the position-tracking accuracy and sensitivity of the ACL system.

In this embodiment, when the axes are orthogonal to one another, a small movement of the distal tip, which is not parallel to any of the axes, translates to a large change in the impedances sensed by all three pairs of electrodes (e.g., electrodes 48A and 48D, electrodes 48B and 48D, and electrodes 48C and 48D), i.e., resulting in the maximal accuracy and sensitivity of the ACL system.

In some cases, the initial placement of electrodes 48A-48D may cause a deviation from orthogonality between the three axes. In such cases, during the mapping and/or ablation procedures, the operator may have to reposition one or more of patches 49A-49D on the body of patient 14, typically carried out by trial and error, so as to improve the accuracy and sensitivity of the ACL system.

Improving ACL Accuracy and Sensitivity Using PCA

Figure 3:
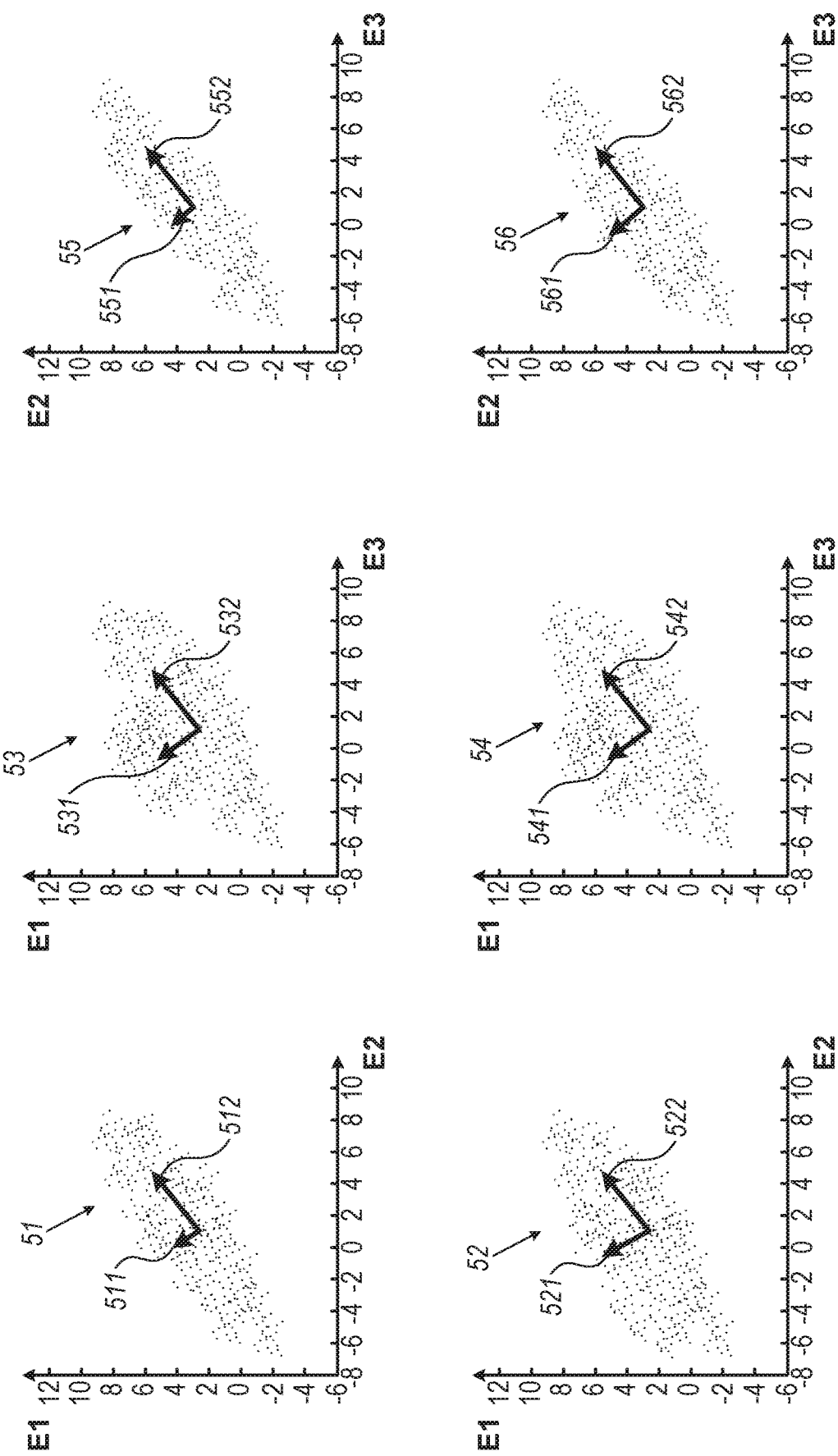
FIG. 3 is a schematic, pictorial illustration of a set of graphs showing principal component analysis of impedance-based data points, in accordance with an embodiment of the present invention.

FIG. 3 is a schematic, pictorial illustration of graphs 51-56 showing principal component analysis (PCA) of impedance-based data points acquired by distal tip 13, in accordance with an embodiment of the present invention.

After the insertion of distal tip 13 into heart 40, the ACL system and the magnetic position tracking system acquire respective measurements indicative of the position of distal tip 13. The coordinate system of the magnetic position tracking system has three axes orthogonal to one another, whereas the angles between the axes of the coordinate system of the ACL system depend on the position of electrodes 48A-48D relative to one another. Note that, even when physician 16 does not move catheter 12, the actual position of distal tip 13 changes relative to electrodes 48A-48D due to cyclical breathing oscillations and heart pulses of patient 14.

As described above, when the axes of the ACL system are orthogonal to one another, the aforementioned movement of distal tip translates to a large change in the impedances sensed by all three pairs of electrodes 48. Any deviation from orthogonality reduces the sensitivity of the ACL system in one or more axes. In some embodiments, processor 20 is configured to receive the impedance-based positions of the data points measured by the ACL sensor of distal tip 13, and to apply the PCA to these impedance-based positions received from. Note that orthogonality between the axes of the ACL system causes a round-shaped distribution of the impedance-based positions, refers to herein as a cloud, whereas a deviation from orthogonality causes an elliptical-shaped distribution of the cloud because of sensitivity differences between the axes of the ACL system.

In some embodiments, processor 20 is configured to display, using graphs 51-56, a correlation between the data points acquired by distal tip 13, between two pairs of electrodes.

In some embodiments, processor 20 is configured to apply the PCA techniques so as to determine a combination of two-dimensional (2D) graphs 51-56, wherein each 2D graph represent a selected projection of a three-dimensional (3D) cluster or cloud of the impedance-based data points acquired by distal tip 13. In essence, the PCA techniques project the 3D cloud of the data points into multiple 2D projections using a transformation, so as to emphasize variation in the accuracy and sensitivity of the ACL system and bring out strong patterns in the data points collected by distal tip 13.

Further details on PCA and use cases of applying PCA are provided, for example, by Wold et al., in "Principal Component Analysis," Chemometrics and Intelligent Laboratory Systems, volume 2 (2005), pages 37-52, published by Elsevier Science Publishers B.V., Amsterdam, which is incorporated herein by reference.

In some embodiments, the data points acquired between electrodes 48A and 48D are referred to herein as "E1," the data points acquired between electrodes 48B and 48D are referred to herein as "E2," and the data points acquired between electrodes 48C and 48D are referred to herein as "E3." For example, graph 51 depicts the dependence between E1 and E2, which is the correlation between the data acquired relative to reference electrode 48D, between electrodes 48A and 48B, respectively.

In some embodiments, graphs 51, 53 and 55 depict the data points acquired using the initial placement of electrodes 48A-48D, shown in FIG. 2 above, and graphs 52, 54 and 56 depict the corresponding data points acquired using a different arrangement of electrodes 48A-48D, e.g., after repositioning electrode 48B, shown in FIG. 4 below.

Reference is now made to graph 51. In some embodiments, processor 20 is configured to apply the PCA on the 3D cloud of the bio-impedance data points, so as to determine a coordinate system comprising axes 511 and 512 on a 2D projection of the data points acquired using E1 and E2. In some embodiments, the coordinate system of axes 511 and 512 begins at the center of gravity of the 2D projection, and axes 511 and 512 are substantially parallel to respective short and long axes (not shown) of the projection having an elliptical shape.

In the context of the present invention, and in the claims, the term "2D cluster" refers to a graph produced by projected a 3D cluster of data points relative to two respective axes of respective graphs 51-56.

In these embodiments, the elliptical-shaped distribution of the data points, shows that after distal tip 13 moves relative to patches 49, the variance of the projected data points is larger along axis 512 compared to the variance along axis 511. The larger variance indicates that the position tracking accuracy and sensitivity of the ACL system is higher in axis 512 compared to axis 511. In other words, graph 51 shows that electrodes 48A, 48B and 48D are arranged in a configuration that causes substantial deviation from orthogonality in the coordinate system of axes 511 and 512. In these embodiments, processor is configured to define that at least one of electrodes 48A, 48B and 48D should be repositioned to an alternative position on the skin of patient 14.

Reference is now made to graph 53, which is a 2D projection of a correlation between E1 and E3, in a coordinate system comprising axes 531 and 532. The shape of the projection is still elliptical, but closer to a circle, as shown by arrows representing axes 531 and 532 that are almost equal in length. In some embodiments, a perfectly round shape of the projection of the data points, is indicative of orthogonality in a coordinate system.

The almost-round shape of graph 53 indicates almost-uniform accuracy and sensitivity of the ACL system in tracking distal tip 13 at any position sensed by electrodes 48A and 48C. In an embodiment, processor 20 is configured to determine that electrodes 48A, 48C and 48D are positioned accurately relative to one another so as to obtain the specified accuracy and sensitivity of the ACL system.

Reference is now made to graph 55, which is a 2D projection of a correlation between E2 and E3 in a coordinate system of axes 551 and 552. In this example, an arrow representing the length of axis 551 is substantially shorter than an arrow representing the length of axis 552. This large difference in the arrows length is indicative of substantial deviation from orthogonality, and therefore, of low accuracy and sensitivity the ACL system in axis 551.

In some embodiments, based on the shape of graph 55, processor 20 is configured to conclude that at least one of electrodes 48B, 48C and 48D has to be repositioned to an alternative position on the skin of patient 14.

As depicted in graph 53, the shape of the projection of the data points shows that electrodes 48A, 48C and 48D are positioned correctly relative to one another. On the other hand graphs 51 and 55 are both displaying E2 data points acquired using electrode 48B, in which there are large differences between the long and short axes of the respective coordinate systems.

In some embodiments, processor 20 is configured to store in a memory the initial positions of electrodes 48A-48D, measured using position signals of the position sensors coupled to respective patches 49A-49D. Processor 20 is further configured to analyze graphs 51, 53 and 55, and, based on the output of the PCA depicted above, to determine that electrode 48B has to be repositioned (in this example).

In an embodiment, processor 20 is configured to evaluate, based on the data points collected using electrodes 48A-48D, and on the respective positions of patches 49A-49D, one or more alternative positions for electrode 48B. In this embodiment, processor 20 is configured to apply a PCA-based transformation on the positions of electrodes 48A-48D, after repositioning electrode 48B.

In some embodiments, processor 20 is configured to apply the PCA to produce graphs 52, 54 and 56, which correspond respectively to graphs 51, 53 and 55, after repositioning electrode 48B. Graphs 52, 54 and 56 may be used, by processor 20 and/or by a user of system 10, to evaluate the uniformity of the accuracy and sensitivity of the ACL system after repositioning electrode 48B.

In an embodiment, physician 16 may move distal tip 13 in a predefined round path within heart 40. In this embodiment, the orthogonality between the axes of the ACL system will determine the shape of the distribution of the impedance-based positions. As described above, any deviation from orthogonality causes elliptical-shaped distribution, whereas full orthogonality typically results in a round-shaped distribution of the impedance-based positions.

Figure 4:
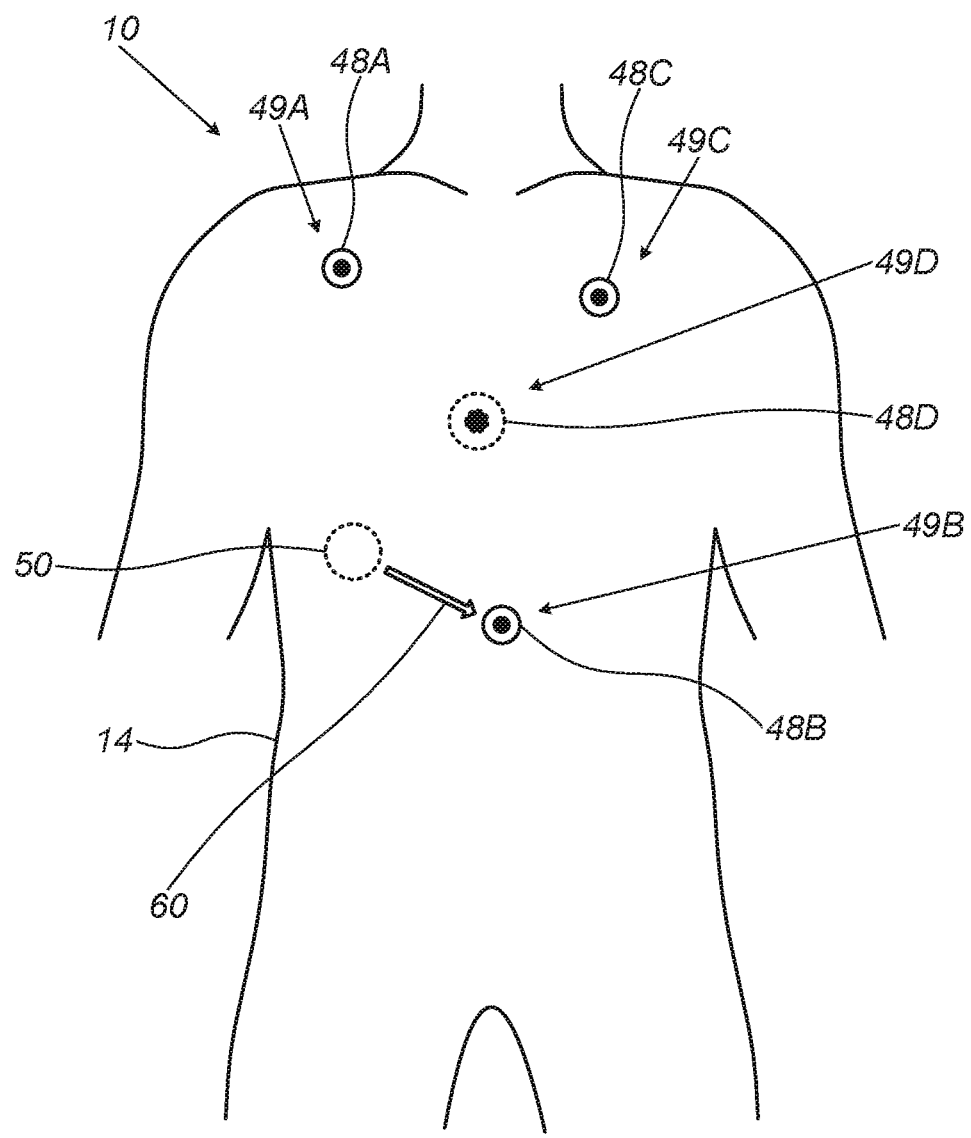

FIG. 4 is a schematic, pictorial illustration of patches 49A-49D attached externally to the body of patient 14, in accordance with another embodiment of the present invention. In some embodiments, processor 20 is configured to evaluate an alternative position for electrode 48B, which is initially located at location 50 on patient 14.

In the example of FIG. 4, processor 20 displays the proposed alternative location of patch 49B, shifted from location 50 by an offset 60, to the position shown in FIG. 4. In an embodiment, processor 20 is configured to carry out a revised PCA based on the proposed alternative location of patch 49B. In this embodiment, processor 20 is configured to apply a transformation on a coordinate system of the 3D cloud of the data points, based on the alternative location of patch 49B (received from the position sensor of patch 49B), so as to evaluate the accuracy and sensitivity of the ACL system after repositioning electrode 48B. In an embodiment, processor 20 is further configured to display an output of the evaluation by displaying projection of the 3D cloud on 2D graphs 52, 54 and 56 of the data points in the transformed coordinate system.

Reference is now made back to FIG. 3. Graph 52 shows the correlation between E1 and E2, and therefore corresponds to graph 51 after repositioning patch 49B and using the revised PCA. In this example, the length of the arrow representing axis 521 of graph 52, appears longer than the length of the arrow representing axis 511 of graph 51, which is indicative of improved accuracy and sensitivity of the ACL system shown in the projection of the data points collected using electrodes 48A, 48B, and 48D.

In some embodiments, graph 56 depicts the correlation between E2 and E3, corresponds to graph 55 after repositioning patch 49B and applying the revised PCA. The shape of graph 56 is closer to a circle compared to the shape of graph 55. In particular, the length of an arrow representing short axis 561 of graph 56 is longer than the length of an arrow representing corresponding axis 551 of graph 55, which is indicative of improved accuracy and sensitivity of the ACL system shown in the projection of the data points collected using electrodes 48B, 48C and 48D.

In some embodiments, graphs 53 and 54 show the correlation between E1 and E3, based on data points acquired using electrodes 48A, 48C and 48D. As depicted in FIG. 4, electrodes 48A and 48C, as well as electrode 48D, are not repositioned, and therefore, the reposition of electrode 48B has no impact on the shape of graph 54 relative to graph 53.

In some embodiments, processor 20 is configured to evaluate the alternative position of electrode 48B, for example, by calculating a ratio between lengths of the arrows representing the axes of one or more graphs among graphs 52, 54 and 56.

In some embodiments, processor 20 is configured to carry out additional improvements in the accuracy and sensitivity of the ACL system, for example, by evaluating the impact of repositioning another electrode among electrodes 48A, 48C and 48D, after repositioning electrode 48B.

In alternative embodiments, processor 20 evaluates the possibility to replace at least one of electrodes 48A-48D, with another electrode coupled to the skin of patient 14. For example, in the configuration depicted in FIG. 1 above, six electrodes 28a-28f are coupled to the skin of patient 14, arranged in three couples. In an embodiment, process may initially use electrodes 28a-28c coupled to the chest of patient 14, and electrode 28d as a reference electrode. In this embodiment, processor 20 is configured to evaluate each electrode 28e and 28f as an alternative reference electrode instead of electrode 28d, and based on a PCA similar to the PCA depicted in FIGS. 2-4 above, to replace electrodes 28d, for example, with electrode 28e that may serve as a reference electrode.

In other embodiments, processor 20 may apply any other suitable configuration of electrodes and any suitable criteria for evaluating and improving the level of accuracy and sensitivity of the ACL system.

Although the embodiments described herein mainly address applying ACL in cardiology procedures, the methods and systems described herein can also be used in other applications, such as in organs having a blood pool.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
an interface, configured to receive signals from a calibration probe inserted in an organ of a patient; and
a processor, configured to:
hold multiple electrode positions corresponding respectively to multiple electrodes attached externally to the patient in a memory;
evaluate, based on the received signals, multiple data points, each data point comprising (i) a respective measured coordinate of the calibration probe, and (ii) a respective set of electrical values indicative of respective impedances between the calibration probe and the multiple electrodes;
evaluate, based on the multiple data points and on the electrode positions, an alternative position for a selected electrode to be repositioned; and
output an identification of the selected electrode and the evaluated alternative position, wherein the data points are representable as a three-dimensional (3D) cluster, and wherein the processor is configured to evaluate the alternative position by projecting the 3D cluster onto a selected two-dimensional (2D) coordinate system, the 2D coordinate system comprises first and second axes, and wherein the processor is configured to evaluate the alternative position by evaluating a 2D cluster produced by projected data points relative to the first and second axes and wherein the 2D cluster comprises an ellipse whose axes are defined by the first and second axes, and wherein the processor is configured to evaluate the alternative position by calculating a ratio between lengths of the first and second axes within the 2D shape.

2. The apparatus according to claim 1, wherein the processor is configured to evaluate the alternative position by applying principal component analysis (PCA) to the data points.

3. The apparatus according to claim 1, wherein the interface is configured to derive the respective measured coordinate of the calibration probe from a signal received from a magnetic position sensor in the calibration probe.

4. A method, comprising:
receiving signals from a calibration probe inserted in an organ of a patient;
holding multiple electrode positions corresponding respectively to multiple electrodes attached externally to the patient;
evaluating, based on the received signals, multiple data points, each data point comprising (i) a respective measured coordinate of the calibration probe, and (ii) a respective set of electrical values indicative of respective impedances between the calibration probe and the multiple electrodes;
evaluating, based on the multiple data points and on the electrode positions, an alternative position for a selected electrode to be repositioned; and
outputting an identification of the selected electrode and the evaluated alternative position, wherein the data points are representable as a three-dimensional (3D) cluster, and wherein evaluating the alternative position comprises projecting the 3D cluster onto a selected two-dimensional (2D) coordinate system, the 2D coordinate system comprises first and second axes, and wherein evaluating the alternative position comprises evaluating a 2D cluster produced by projected data points relative to the first and second axes and the 2D cluster comprises an ellipse whose axes are defined by the first and second axes, and wherein evaluating the alternative position comprises calculating a ratio between lengths of the first and second axes within the 2D shape.

5. The method according to claim 4, wherein evaluating the alternative position comprises applying principal component analysis (PCA) to the data points.

6. The method according to claim 4, wherein receiving the signals comprises deriving the respective measured coordinate of the calibration probe from a signal received from a magnetic position sensor in the calibration probe.

* * * * *